United States Patent [19]
Berry

[11] 3,964,867
[45] June 22, 1976

[54] REACTION CONTAINER

[75] Inventor: John Franklin Berry, Houston, Tex.

[73] Assignee: Hycel, Inc., Houston, Tex.

[22] Filed: Feb. 25, 1975

[21] Appl. No.: 553,008

[52] U.S. Cl. ............................ 23/253 R; 23/259; 23/292; 356/246
[51] Int. Cl.² ............... G01N 33/16; G01N 21/24; B65D 79/02
[58] Field of Search ............... 23/253, 259, 292; 356/246

[56] References Cited
UNITED STATES PATENTS

| | | | |
|---|---|---|---|
| 3,286,583 | 11/1966 | Ferrari | 23/292 |
| 3,350,946 | 11/1967 | Isreeli | 23/253 X |
| 3,718,439 | 2/1973 | Rosse et al. | 356/246 X |

Primary Examiner—R. E. Serwin
Attorney, Agent, or Firm—Timothy L. Burgess; Robert P. Cogan

[57] ABSTRACT

A mold formed reaction container includes a lower portion having four sides forming an open top parallelepiped structure and an upper portion in the shape of a threaded hollow cylinder over which a cap may be screwed. The lower portion is inserted in a square opening of an automatic chemical analyzer so that two of the sides thereof are in a radiant energy path. The opening of the analyzer has two slot indentions removed from two opposite sides thereof and the lower portion of the container has two corresponding key extensions therefrom to insure the proper two sides of the container are placed in the energy path. Further, one of the sides of the container not having a key extension has a label on a portion thereof and that portion intersects and blocks a second radiant energy path through the opening in such a manner that the insertion of the container can be detected.

14 Claims, 4 Drawing Figures

REACTION CONTAINER

This invention relates to a container, and more particularly to a container for holding chemical reagents and a specimen to be tested in which a detectable reaction occurs while the container is inserted in a chemical analyzer.

In the past, an automatic chemical analyzer for selectively and simultaneously performing a plurality of STAT chemical tests on blood serum has been developed and is shown in U.S. patent application Ser. No. 406,258, filed on Oct. 15, 1973, now U.S. Pat. No. 3,873,273, issued Mar. 25, 1975 in the name of John J. Moran, et al., and assigned to the present assignee. In that analyzer, of that patent application, pre-packaged containers of different chemical reagents are utilized in performing the various tests, with each different package being for detecting a different given substance in blood. To perform a test, the serum is separated from the blood by known laboratory techniques and a precise amount of serum is added to the reagent for the particular substance desired to be detected. At this point, the container and specimen mixture is inserted in the analyzer shown by the above mentioned Moran et al., patent application and a given time after the insertion of the container, the contents thereof are analyzed by measuring the radiant energy absorbance of a specific wavelength of radiant energy, thereby. In certain instances, the contents of the container are analyzed in the above manner at two separate times to arrive at the desired result.

It has been found that a more accurate optical reading is obtained by using a container with a flat area positioned perpendicular to the optical path. Such a container could be for instance, an open topped parallelepiped configuration and the opening in the analyzer would be an open topped parallelepiped configuration into which the container is inserted. Such an arrangement is shown in U.S. Patent application Ser. No. 435,227 in the name of George T. Mioduski, filed Jan. 21, 1974, now U.S. Pat. No. 3,882,318, and assigned to the present assignee. It has been found that it is difficult to properly configure a flat sided container out of glass. Accordingly, it has been found necessary to fabricate such a container out of a clear plastic material, which plastic material must be nonflorescent and capable of transmitting ultraviolet radiant energy, such as Plexiglas. The fabrication of the container requires care in insuring that the two surfaces thereof which the optical path intersects are free from scratches, mold lines or other imperfections which may tend to contaminate the radiant energy transmitted through the container. Further, the two surfaces which the optical path intersects must be a precise distance apart to insure consistent analysis.

Because it is desired that the reading be made at a specific time or at specific times, measured from the insertions of the container into the analyzer, it is necessary to provide some means to detect the insertion of the container. As shown in the above mentioned Mioduski patent application, a radiant energy beam through the chamber to a phototransistor is broken by the insertion of the container to thereby, provide a signal to control circuitry included in the analyzer to begin measuring the time. In the case of the clear plastic container, it is necessary that a portion thereof blocks the energy beam to the phototransistor.

In accordance with one preferred embodiment of this invention, there is provided a singular reaction container of a nonflorescent, visible and ultraviolet radiant energy transmitting material for insertion in an automatic chemical analyzer. The analyzer causes energy to be applied through an energy path, with the container intersecting the energy path when inserted in the analyzer. The container comprises four sides at least two of which are parallel, and a fixed distance apart. At least one of the sides has an extension therefrom to correspond to an indention in the analyzer. The extension is placed on the container to position the two parallel sides to intersect the energy path when the container is inserted in the analyzer with the extension inserted in the indention.

There is described hereafter a detailed description of one preferred embodiment of this invention, with specific reference being made to the following FIGURES, in which.

Figure 1:
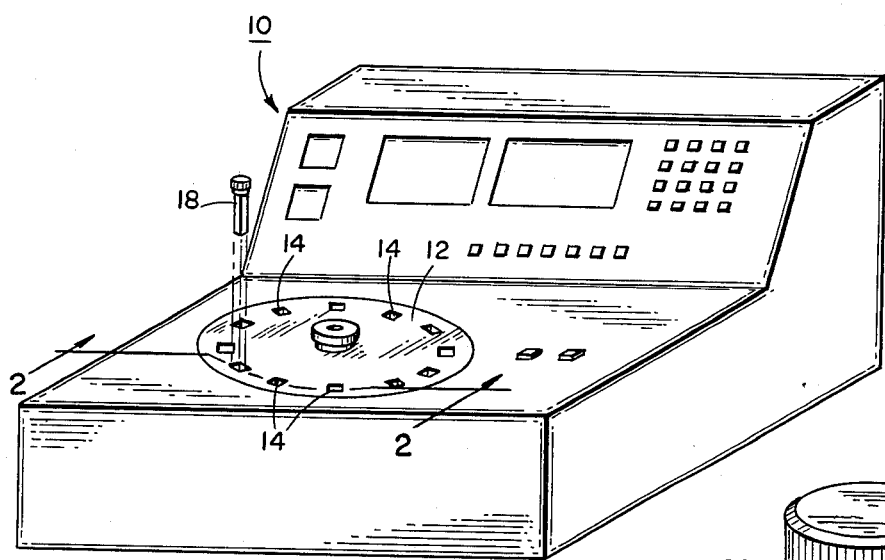
FIG. 1 is a prospective view of the automatic analyzer showing the testing area and the chambers therein for receiving the containers to the tested.

Referring now to FIG. 1, an automatic analyzer 10 is shown generally. For a more specific explanation of analyzer 10, reference is made to the above mentioned Moran et al. patent application. Analyzer 10 includes a circular shaped testing area 12, in which a plurality of open faced parallelepiped chambers 14 are positioned around the periphery of area 12. Each of the chambers 14 includes a pair of key slots 16 on the sides of the chambers 14 which are approximately perpendicular to the axis of area 12.

As explained in the above mentioned Moran et al. patent application, each of the chambers 14 is used to perform one test, that is, to detect one substance in blood serum. There is a specific reagent assigned to each channel, and each reagent is included in a container 18 which is predesignated to be inserted in one of the chambers 14. When it is desired to perform a test for a specific substance, the reagent container 18 for that substance is selected and a prescribed amount of blood serum is placed therein. Then, the mixture in the selected container 18 is inserted in the proper one of the chambers 14, and control circuitry included within analyzer 10 (not shown) which is more fully explained in the above mentioned Moran et al. patent application, records the time that container 18 is inserted. At a specific time or specific times thereafter the control circuitry measures the then radiant energy absorbance of the contents in the selected container 18. It should be noted that reaction area 12 includes a heating block which is maintained at 37°C., or body temerpature, to cause the reaction to occur in a predictable manner that may be programmed into the control circuitry of analyzer 10.

Figure 2:
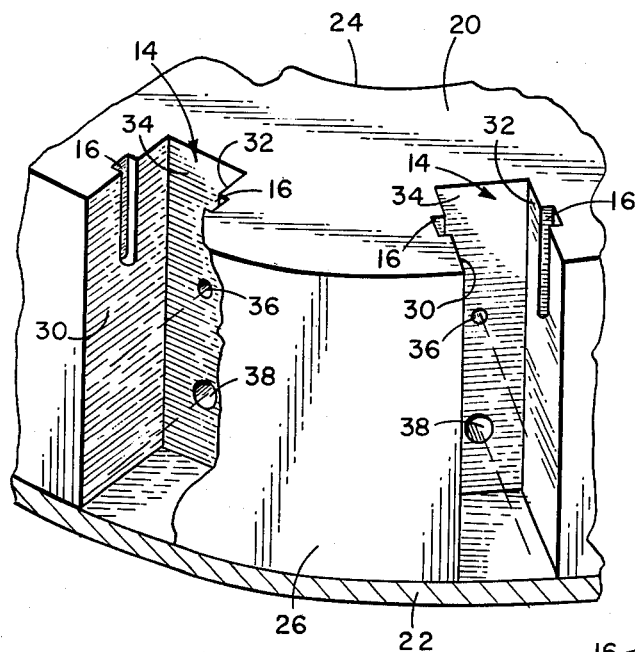
FIG. 2 is a view taken through lines 2—2 shown in FIG. 1.

Referring now to FIG. 2, the heating block of sample area 12 is shown, as taken across lines 2—2 of FIG. 1. FIG. 2 includes the heating block 20, which is situated in analyzer 10 on a base 22. Block 20 may be configured from a hollow cylinder having an inner surface 24 and an outer surface 26 and may be made of aluminum. A plurality of perpendicular shaped indention areas are machined from outer surface 26 and each forms three sides of a chamber 14. The fourth side of chamber 14 may be formed by a sleeve (not shown), which fits around the outer surface 26 of block 20, and would contain the optical detector for measuring the radiant energy absorbance of the container 18 contents and the phototransistor for detecting the presence of a container 18 in chamber 14. Such elements are shown by the above mentioned Mioduski Patent Application.

Each of the chambers 14 includes a slot indention 16 on each of the sides 30 and 32 thereof. On the back 34 of each of the partially formed chambers 14 are two openings 36 and 38, which are holes to back side 34 from inner surface 24 of block 20. Within the area formed by inner surface 24 is a xenon lamp (not shown) which provides visible and ultraviolet radiant energy through each of openings 36 and 38, whereby openings 36 and 38 constitute a pair of energy paths.

As shown in the above mentioned Mioduski patent application, a phototransistor may be positioned in juxtaposition with block 20 to be in alignment with hole 36 and is used to detect the presence of a container 18 in the chamber 14 by providing an electrical signal whenever less than a specific amount of radiant energy is applied thereto due to the container 18 blocking the energy path. Similarly, a PIN diode may be positioned in alignment with hole 38 to detect the radiant energy absorbance of the contents of container 18 when it is inserted in chamber 14.

Figure 3:
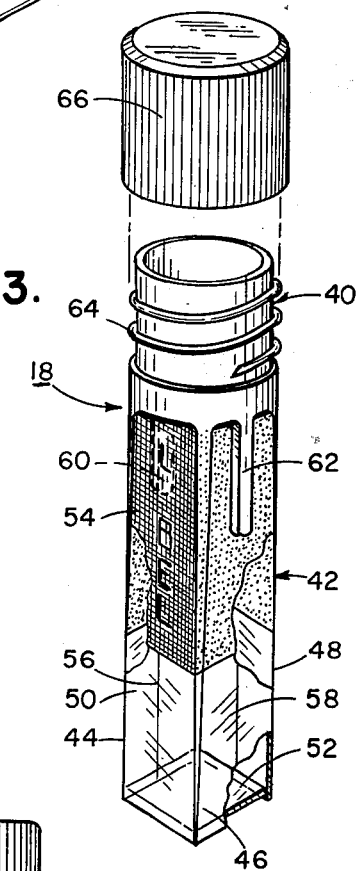
FIG. 3 is an isometric view of the container to be inserted in the chambers shown in FIG. 1.

Referring now to FIG. 3, a detailed drawing of container 18 is shown. Container 18 is fabricated by known molding techniques of a nonflorescent, visible and ultraviolet radiant energy transmitting plastic material, such as Plexiglas, and includes an upper portion 40 in the shape of a hollow cylinder having an open top and an open bottom, and a lower portion 42 in the shape of a parallelepiped having an open top, that is, a geometric configuration having a first pair of parallel sides 44 and 46 and a second pair of parallel sides 48 and 50, and a bottom 52. The diagonal of the square formed by sides 44, 46, 48 and 50 is equal to the diameter of the upper portion cylinder 40. Bottom, 52, is positioned slightly above the lower end of each of the sides, 44, 46, 48 and 50 to form a base of container 18.

On each of the three sides 44, 46 and 48, approximately the upper 60 percent of the surface is opaque and approximately the lower 40 percent of the surface is clear. The surface of the sides 44, 46 and 48 may be made opaque by properly preparing the mold in which the container 18 is formed so that the upper 60 percent opaque area is a rough surface, and the lower 40 percent clear area is a smooth surface.

The forth side 50 is clear and a nontransparent label 54 is affixed to the portion of side 50 constituting the upper 60 percent. This label 54 may serve to identify the reagents in container 18 and, as explained hereafter, is positioned to intersect a light path and block the light therethrough. Label 54 may be a printed gum backed label affixed to side 50 or may be silk screened on side 50 in a conventional manner.

Container 18 is formed of plastic using a mold fabrication technique and thus, a pair of mold lines 56 and 58 may appear on respective sides 44 and 46. It is necessary that the mold lines 56 and 58 are not placed in the optical path from hole 38 because they would tend to distort the radiant energy absorbance measured.

Further, it is necessary to maintain a precise distance between the two parallel sides 48 and 50 intersecting the radiant energy path and to maintain the clear area of sides 48 and 50 free from scratches and other imperfections. Thus, extreme care must be used in polishing the mold to maintain the precise distance and freedom from scratches and other imperfections for the clear areas of the sides intersecting the radiant energy path. In order to reduce this care, it is desirable to always have the same two sides 48 and 50 as the ones intersecting the optical path. Thus only two of the four clear areas in the mold must be maintained. This is especially true when several molds are utilized to produce a large volume of containers 18 and the product of each mold must be nearly identical in the distance between the sides.

Accordingly, a pair of key extensions 60 and 62, are provided from the top of lower portion 72 on each of sides 44 and 46 and positioned at the center of each of sides 44 and 46. The key extensions 60 and 62 are designed to be inserted into the slot indentions 16 in chambers 14 shown in FIGS. 1 and 2. Thus, it is seen that the mold lines 56 and 58 when container 18 is inserted in chamber 14 with the keys 60 and 62 in the slots 16 will be along the sides 30 and 32 thereof and thus remote from radiant energy path through the hole 38. Further, since the sides 48 and 50 will be the only ones in the radiant energy path, the required care in maintaining the mold is necessary for only two sides rather than all four.

Figure 4:
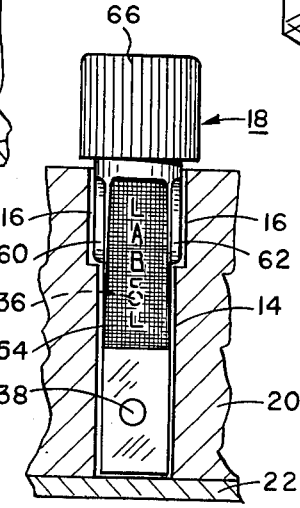
FIG. 4 shows the container when inserted in the chamber.

The exact positioning of label 54 on side 50 of container 18 is not critical so long as, when container 18 is completely inserted in chamber 14, label 54 intersects the light path out of hole 36 and the clear area of sides 48 and 50 intersect the light path out of hole 38. Thus, the bottom of label 54 may begin at any point between the holes 36 and 38 when container 18 is completely inserted in chamber 14, as shown in FIG. 4.

The lower portion 42 of container 18 is of a height at least as great as the height of chamber 14. Thus, the upper portion 40 of the container 18 will extend above block 20 when container 18 is inserted in chamber 14. The upper portion 40, as previously mentioned, is cylindrical in shape and has threads 64 molded therein. A top 66 may be screwed over upper portion 40 of container 18 to maintain an airtight seal therefore until such time as the contents are to be mixed with the specimen.

What is claimed is:

1. A singular reaction container of a nonflorescent, visible and ultraviolet radiant energy transmitting material for insertion in an automatic chemical analyzer, said analyzer causing energy to be applied through first and second energy paths, said first path being for measuring a chemical reaction occurring in said container and said second path being for detecting the insertion of said container in said analyzer, said container intersecting said first energy path when inserted in said analyzer, said container comprising four sides, two of which are parallel and a fixed distance apart, at least one of said sides having an extension therefrom to correspond to an indention in said analyzer, said extension being placed to position said two parallel sides to intersect said energy path when said container is inserted in said analyzer with said extension inserted in said indention, at least one of said two parallel sides includes a nontransparent area remote from the portion of that side which intersects said energy path, and positioned on that side to intersect only said second path when said container is inserted in said analyzer.

2. The invention according to claim 1 wherein said container further includes a bottom, said four sides and bottom forming an open top parallelepiped configuration.

3. The invention according to claim 2 wherein said container further includes an open ended cylindrical portion affixed to the open end of said parallelepiped configuration for holding a label.

4. The invention according to claim 2 wherein said remaining two sides contain mold lines thereon.

5. The invention according to claim 2 wherein said nontransparent area includes a label on that portion of that side.

6. In an automatic chemical testing system in which a container containing a sample to be tested and a reagent is inserted into a chamber portion of said system, said system including optical energy providing means and a pair of energy paths to and through said chamber positioned to intersect respective first and second portions of said container when inserted in said chamber, said chamber including a portion thereof having an indention slot removed therefrom, said container comprising:

a singular molded nonflorescent, visible and ultraviolet radiant energy transmitting member having a first pair of substantially parallel sides and a second pair of substantially parallel sides which are substantially perpendicular to said first pair of sides, said second pair of sides being a precise distance apart;

a key extension from one of said sides and positioned to fit in said slot when said container is inserted in said chamber, said one side having said key extension being selected so that when said key is inserted in said slot and said container is completely inserted in said chamber, the second pair of sides of said container are aligned in said chamber to intersect said energy paths; and nontransparent area on at least one of second pair of sides, said nontransparent area being positioned on said one side to intersect one of said energy paths and not intersect the other energy path when said key is inserted in said slot and said container is completely inserted in said chamber.

7. The invention according to claim 6 is in which said chamber is an open top parallelepiped having first and second pairs of parallel sides, configured in overall dimensions such that said container fits therein, said energy paths extending between said second pair of sides, each side of said first pair of sides having a slot indention downward from the open end of said parallelepiped and positioned at the center thereof between said first pair of sides, wherein said container further includes a key extension from each of said sides of said first pair of container sides and positioned thereon to be centered between said second pair of container sides.

8. The invention according to claim 7 wherein said nontransparent area is on one of said second pair of container sides.

9. The invention according to claim 8 wherein said one of said second pair of sides includes a label to cause said nontransparent area.

10. The invention according to claim 8 wherein said container further includes an open end cylindrical portion extending from said open end of said parallelepiped, said parallelepiped and cylinder portions having such dimensions that when said container is inserted in said chamber, said cylinder portion remains above said chamber.

11. The invention according to claim 10 wherein said cylindrical portion has threads thereon positioned to receive a cap.

12. The invention according to claim 10 wherein the diameter of said cylinder portion equals the diagonal axis across the open top of said parallelepiped portion.

13. The invention according to claim 12 wherein each of said first pair of sides has a mold line therein.

14. The invention according to claim 6 wherein the material of said member is Plexiglas.

* * * * *